(12) United States Patent
Kim et al.

(10) Patent No.: US 11,753,647 B2
(45) Date of Patent: Sep. 12, 2023

(54) ISOLATED POLYNUCLEOTIDE INCLUDING PROMOTER REGION, HOST CELL INCLUDING THE SAME AND METHOD OF EXPRESSING A TARGET GENE USING THE HOST CELL

(71) Applicant: Samsung Electronics Co., Ltd., Suwon-si (KR)

(72) Inventors: Jae-Young Kim, Suwon-si (KR); Taeyong Kim, Daejeon (KR); Seung Hoon Song, Suwon-si (KR); Woo Yong Shim, Suwon-si (KR); Yu Kyung Jung, Hwaseong-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 129 days.

(21) Appl. No.: 17/151,746

(22) Filed: Jan. 19, 2021

(65) Prior Publication Data
US 2022/0025386 A1     Jan. 27, 2022

(30) Foreign Application Priority Data
Jul. 24, 2020 (KR) .................. 10-2020-0092546

(51) Int. Cl.
*C12N 15/74* (2006.01)
*C12N 1/20* (2006.01)
*C12N 15/70* (2006.01)

(52) U.S. Cl.
CPC ............. *C12N 15/74* (2013.01); *C12N 1/20* (2013.01); *C12N 15/70* (2013.01)

(58) Field of Classification Search
CPC ........... C12N 15/74; C12N 1/20; C12N 15/70
See application file for complete search history.

(56) References Cited

U.S. PATENT DOCUMENTS

| | | | |
|---|---|---|---|
| 6,137,029 A | 10/2000 | Tubert et al. | |
| 8,114,665 B2 | 2/2012 | Wu et al. | |
| 8,431,373 B2 | 4/2013 | Yi et al. | |
| 2011/0256524 A1 | 10/2011 | Lee et al. | |
| 2020/0407730 A1 | 12/2020 | Park et al. | |

FOREIGN PATENT DOCUMENTS

| | | |
|---|---|---|
| KR | 20050058990 A | 6/2005 |
| KR | 20070108155 A | 11/2007 |
| KR | 20100024055 A | 3/2010 |
| KR | 101877303 B1 | 7/2018 |
| WO | 1995025169 A1 | 9/1995 |

OTHER PUBLICATIONS

Mice C. Ind, et al., "Inducible-Expression Plasmid for Rhodobacter sphaeroides and Paracoccus denitrificans," Applied and Environmental Microbiology, Oct. 2009, pp. 6613-6615, vol. 75, No. 20.
Dariusz Bartosik, et al., "Identification of the Partitioning Site within the repABC-Type Replicon of the Composite Paracoccus versutus Plasmid pTAV1," Journal of Bacteriology, Nov. 2001, pp. 6234-6243, vol. 183, No. 21.
Haihan Zhanga et al.,"Paracoccus versutus KS293 adaptation to aerobic and anaerobic denitrification: Insights from nitrogen removal, functional gene abundance, and proteomic profiling analysis," Bioresource Technology, Mar. 31, 2018, pp. 321-328, vol. 260.
Michael B. Elowitz et al., "Photoactivation turns green fluorescent protein red," Current Biology, Oct. 1, 1997, pp. 809-812, vol. 7, No. 10.
Promoters, Jan. 13, 2021, pp. 1-3, https://www.addgene.org/mol-bio-reference/promoters/.
Simon C. Baker et al., "Molecular Genetics of the Genus Paracoccus: Metabolically Versatile Bacteria with Bioenergetic Flexibility," Microbiology and Molecular Biology Reviews, Dec. 1998, pp. 1046-1078, vol. 62, No. 4.

*Primary Examiner* — Robert A Zeman
(74) *Attorney, Agent, or Firm* — CANTOR COLBURN LLP (57) ABSTRACT

An isolated polynucleotide including a promoter region derived from a bacterium of the genus *Paracoccus*, a recombinant host cell including the isolated polynucleotide, and a method of expressing a target gene by culturing a recombinant host cell comprising a polynucleotide comprising the promoter region and a target gene operably linked to the promoter region, under conditions in which the target gene is expressed.

16 Claims, 3 Drawing Sheets
Specification includes a Sequence Listing.

SEQUENCE LISTING

```
<160> NUMBER OF SEQ ID NOS: 15

<210> SEQ ID NO 1
<211> LENGTH: 175
<212> TYPE: DNA
<213> ORGANISM: Paracoccus versutus

<400> SEQUENCE: 1
aagggccttt gtgacgtttt cccgaagcca agaccacgat ccgacaaatg attgcgctaa      60
ccgtgtctga ttgcgctaac cctgcccata tgtgcgcttt cgccggggaa atgccgtgtt     120
ataggacgcg caacggccgc tgccggcccg gactatcagc aggagcaaag gtgcc          175

<210> SEQ ID NO 2
<211> LENGTH: 660
<212> TYPE: DNA
<213> ORGANISM: Paracoccus versutus
```

<400> SEQUENCE: 2

```
ctttcgtgca aatccgtatc cgcccggcca gcgacaaggt attgcaacag tattgacgca      60
agatgaacgc ggccggcccc aaggacaagg ggcacggacc tgcccattag gtcaagccgc     120
cggtcgggcg gcagccggtc gggctcgggg cgcgccagat cgaccgccag ggccagctcg     180
accgggccat gcggcgcggc atgcaggatg cccacccccc gcgcctcgat cctgccgcgg     240
atcgaatcgg gcgcatcggc gaggatccga ccgcctcgc ggcgcaggac ggtgcggtcg      300
tccgccacca gcgccgcgcc aagcgccatc atctgcagcg ccagcacgga cttccccgcg     360
cccgagggcc ccaggatcag cagccccgt tccggtggg cgatgcagct tgcatgcagg       420
atcatggctt ccttcccctt gcctcttgcc gcggcgcgaa tcgccccgga ccctacgcc      480
ggaccaaggg cctttgtgac gttttcccga agccaagacc acgatccgac aaatgattgc     540
gctaaccgtg tctgattgcg ctaaccctgc ccatatgtgc gctttcgccg gggaaatgcc     600
gtgttatagg acgcgcaacg gccgctgccg gcccggacta tcagcaggag caaaggtgcc     660
```

<210> SEQ ID NO 3
<211> LENGTH: 225
<212> TYPE: PRT
<213> ORGANISM: Artificial
<220> FEATURE:
<223> OTHER INFORMATION: monomeric RFP

<400> SEQUENCE: 3

```
Met Ala Ser Ser Glu Asp Val Ile Lys Glu Phe Met Arg Phe Lys Val
1               5                   10                  15

Arg Met Glu Gly Ser Val Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Ala Tyr Val Lys His Pro Ala Asp Ile Pro
65                  70                  75                  80

Asp Tyr Leu Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Glu Phe Ile Tyr Lys Val Lys Leu Arg Gly Thr Asn
        115                 120                 125

Phe Pro Ser Asp Gly Pro Val Met Gln Lys Lys Thr Met Gly Trp Glu
    130                 135                 140

Ala Ser Thr Glu Arg Met Tyr Pro Glu Asp Gly Ala Leu Lys Gly Glu
145                 150                 155                 160

Ile Lys Met Arg Leu Lys Leu Lys Asp Gly Gly His Tyr Asp Ala Glu
                165                 170                 175

Val Lys Thr Thr Tyr Met Ala Lys Lys Pro Val Gln Leu Pro Gly Ala
            180                 185                 190

Tyr Lys Thr Asp Ile Lys Leu Asp Ile Thr Ser His Asn Glu Asp Tyr
        195                 200                 205

Thr Ile Val Glu Gln Tyr Glu Arg Ala Glu Gly Arg His Ser Thr Gly
    210                 215                 220

Ala
225
```

<210> SEQ ID NO 4
<211> LENGTH: 677
<212> TYPE: DNA
<213> ORGANISM: Artificial
<220> FEATURE:
<223> OTHER INFORMATION: gene for mRFP

<400> SEQUENCE: 4

```
atggcttcct ccgaagacgt tatcaaagag ttcatgcgtt tcaaagttcg tatggaaggt      60
tccgttaacg gtcacgagtt cgaaatcgaa ggtgaaggtg aaggtcgtcc gtacgaaggt     120
acccagaccg ctaaactgaa agttaccaaa ggtggtccgc tgccgttcgc ttgggacatc     180
ctgtccccgc agttccagta cggttccaaa gcttacgtta acacccggc tgacatcccg      240
gactacctga aactgtcctt cccggaaggt ttcaaatggg aacgtgttat gaacttcgaa     300
gacggtggtg ttgttaccgt tacccaggac tcctccctgc aagacggtga gttcatctac     360
aaagttaaac tgcgtggtac caacttcccg tccgacggtc cggttatgca gaaaaaaacc     420
atgggttggg aagcttccac cgaacgtatg tacccggaag acggtgctct gaaaggtgaa     480
atcaaaatgc gtctgaaact gaaagacggt ggtcactacg acgctgaagt taaaaccacc     540
tacatggcta aaaaaccggt tcagctgccg ggtgcttaca aaccgacat caaactggac      600
atcacctccc acaacgaaga ctacaccatc gttgaacagt acgaacgtgc tgaaggtcgt     660
cactccaccg gtgctta                                                    677
```

<210> SEQ ID NO 5
<211> LENGTH: 39
<212> TYPE: DNA
<213> ORGANISM: Artificial
<220> FEATURE:
<223> OTHER INFORMATION: primer

<400> SEQUENCE: 5

```
gctaaggaag ctaaagacat cgcccgcatc ctgcgcgag                             39
```

<210> SEQ ID NO 6
<211> LENGTH: 24
<212> TYPE: DNA
<213> ORGANISM: Artificial
<220> FEATURE:
<223> OTHER INFORMATION: primer

<400> SEQUENCE: 6

```
aggtttcctc cgccgctgat gatg                                             24
```

<210> SEQ ID NO 7
<211> LENGTH: 35
<212> TYPE: DNA
<213> ORGANISM: Artificial
<220> FEATURE:
<223> OTHER INFORMATION: primer

<400> SEQUENCE: 7

```
gctaaggaag ctaaaccagc agcttattcc acatc                                 35
```

<210> SEQ ID NO 8
<211> LENGTH: 36
<212> TYPE: DNA
<213> ORGANISM: Artificial
<220> FEATURE:
<223> OTHER INFORMATION: primer
```

```
<400> SEQUENCE: 8
ttcggaggaa gccatgctca tgtcccttc atgttg                         36

<210> SEQ ID NO 9
<211> LENGTH: 35
<212> TYPE: DNA
<213> ORGANISM: Artificial
<220> FEATURE:
<223> OTHER INFORMATION: primer

<400> SEQUENCE: 9
gctaaggaag ctaaactttc gtgcaaatcc gtatc                         35

<210> SEQ ID NO 10
<211> LENGTH: 38
<212> TYPE: DNA
<213> ORGANISM: Artificial
<220> FEATURE:
<223> OTHER INFORMATION: primer

<400> SEQUENCE: 10
ttcggaggaa gccatggcac ctttgctcct gctgatag                      38

<210> SEQ ID NO 11
<211> LENGTH: 26
<212> TYPE: DNA
<213> ORGANISM: Artificial
<220> FEATURE:
<223> OTHER INFORMATION: primer

<400> SEQUENCE: 11 ttttttaag gcagttattg gtgccc                                    26

<210> SEQ ID NO 12
<211> LENGTH: 26
<212> TYPE: DNA
<213> ORGANISM: Artificial
<220> FEATURE:
<223> OTHER INFORMATION: primer

<400> SEQUENCE: 12
tttagcttcc ttagctcctg aaaatc                                   26

<210> SEQ ID NO 13
<211> LENGTH: 39
<212> TYPE: DNA
<213> ORGANISM: Artificial
<220> FEATURE:
<223> OTHER INFORMATION: primer

<400> SEQUENCE: 13
cggcggagga aacctatggc ttcctccgaa gacgttatc                     39

<210> SEQ ID NO 14
<211> LENGTH: 38
<212> TYPE: DNA
<213> ORGANISM: Artificial
<220> FEATURE:
<223> OTHER INFORMATION: primer

<400> SEQUENCE: 14
actgccttaa aaaaataagc accggtggag tgacgacc                      38

<210> SEQ ID NO 15
<211> LENGTH: 24
```

```
<212> TYPE: DNA
<213> ORGANISM: Artificial
<220> FEATURE:
<223> OTHER INFORMATION: primer

<400> SEQUENCE: 15
atggcttcct ccgaagacgt tatc                                              24
```

ISOLATED POLYNUCLEOTIDE INCLUDING PROMOTER REGION, HOST CELL INCLUDING THE SAME AND METHOD OF EXPRESSING A TARGET GENE USING THE HOST CELL

CROSS-REFERENCE TO RELATED APPLICATION

This application claims priority to Korean Patent Application No. 10-2020-0092546, filed on Jul. 24, 2020, in the Korean Intellectual Property Office, and all the benefits accruing therefrom under 35 U.S.C. § 119, the content of which is incorporated by reference herein in its entirety.

BACKGROUND

1. Field

The present disclosure relates to an isolated polynucleotide including a promoter region derived from a bacterium of the genus *Paracoccus*, a host cell including the isolated polynucleotide, and a method of expressing a target gene using the host cell.

2. Description of Related Art

A promoter is required for expression of a target gene in a microorganism. The promoter is a region to which RNA polymerase binds to initiate transcription of DNA into mRNA. The binding of RNA polymerase and/or other transcription factors to the promoter, and the strength of the binding, are determined by the DNA sequence and the length of the promoter. In other words, the promoter determines the strength of binding and the conditions under which the gene is expressed. Therefore, to improve expression of a protein in a microorganism in a desired manner, it is important to utilize a promoter capable of expressing a target gene at a desired strength.

Among microorganisms, bacteria are used to produce useful products. Bacteria include Gram-negative and Gram-positive bacteria. Gram-negative bacteria include the genera *Paracoccus* and *Escherichia*. Microorganisms of the genus *Paracoccus* belong to the family Rhodobacteraceae, which are microorganisms having a denitrification function, i.e., reduce nitrogen oxides to N2 through a dissimilatory reduction process.

Accordingly, there is a demand for a strong promoter which may be used to produce useful products from bacteria.

SUMMARY

An aspect provides an isolated polynucleotide including a promoter region including the nucleotide sequence of SEQ ID NO: 1.

Another aspect provides a host cell including the isolated polynucleotide.

Still another aspect provides a method of expressing a target gene using the host cell.

Additional aspects will be set forth in part in the description which follows and, in part, will be apparent from the description, or may be learned by practice of the presented embodiments of the disclosure.

An aspect provides an isolated polynucleotide including a promoter region including the nucleotide sequence of SEQ ID NO: 1.

The terms "promoter" or "promoter region" refer to a DNA region to which regulatory elements such as an RNA polymerase binds in order to initiate transcription of a gene operably linked to the promoter. The sequence of the promoter may be modified as desired to provide a promoter variant having the same or similar or increased activities as the promoter. Thus, a promoter having a nucleotide sequence identity of, for example, 70% or greater, 80% or greater, 90% or greater, 95% or greater, or 97% or greater, or 99% or greater, to the nucleotide sequence of SEQ ID NO: 1 may be also included in the scope of the present disclosure. In an aspect, the promoter region has a nucleotide sequence which is 100% identical to SEQ ID NO: 1 or SEQ ID NO: 2.

The isolated polynucleotide may consist of the nucleotide sequence of SEQ ID NO: 1 or the nucleotide sequence of SEQ ID NO: 2.

The isolated polynucleotide may be a vector comprising the promoter region. In the isolated polynucleotide, a target gene may be operably linked to the promoter region. In the isolated polynucleotide, a target gene may also be operably linked to other expression regulatory sequences in addition to the promoter region. The other expression regulatory sequences may include an operator, a terminator, a transcription activator, a ribosome binding site, or a combination thereof. The target gene may be downstream of and operably linked to the promoter region. The term "operably linked" means that a target gene to be expressed is functionally linked to the promoter sequence so that transcription of the target gene occurs. The vector may further include a replication origin, a promoter control site, a ribosome binding site, a transcription termination site, a selection marker, or a combination thereof, as well as the promoter or a variant thereof and the target gene.

The term "vector", as used herein, refers to an artificial nucleic acid molecule (polynucleotide) including one or more functional units, and which is capable of transferring another nucleic acid (or nucleic acids) linked thereto to a host cell. In view of the nucleotide sequence that mediates the introduction of a particular gene, the terms "vector" "nucleic acid construct" or "expression cassette" can be used interchangeably. The vector may include, for example, a plasmid, a cosmid, a bacteriophage, a vector derived from a virus, etc. The plasmid refers to an extrachromosomal circular, double-stranded DNA loop to which additional DNAs may be linked. The vector used herein may include, for example, a plasmid expression vector, a viral expression vector, and a viral vector capable of performing a function equivalent thereto. In the viral vector, additional DNA may be linked to the viral genome. Certain vectors are designed for autonomous replication in a specific type of host cell into which they are introduced (e.g., a bacterial vector includes a bacterial origin of replication). Other vectors are integrated into the genome of a host cell upon introduction into the host cell, and are thereby replicated along with the host genome. Moreover, certain vectors may direct expression of genes to which they are operatively linked. Such vectors are referred to herein as "expression vectors". In general, an expression vector useful in recombinant DNA techniques is often in the form of a plasmid. The vector used herein may be an expression vector such as, for example, a plasmid expression vector, a viral expression vector, and a viral vector capable of performing a function equivalent thereto.

The vectors, for example, expression vectors, include one or more regulatory sequences, which are selected on the basis of the host cell to be used for expression, and are operatively linked to the nucleic acid sequence to be expressed. "Operatively linked" means that the nucleotide sequence of interest (target gene) is linked to the regulatory sequence(s) in a manner which allows for expression of the nucleotide sequence in the host cell. The term "regulatory sequence" is intended to include a promoter, an enhancer, and other control elements (e.g., polyadenylation signal). Regulatory sequences include those which direct constitutive expression of a target nucleic acid in many types of host cells and those which direct expression of the target nucleic acid only in particular host cells (e.g., tissue-specific regulatory sequences). It will be appreciated by those skilled in the art that design of the expression vector may depend on factors such as selection of the host cell to be transformed/transfected, an expression level of a target protein desired, or the like. The expression vector of the present disclosure may be introduced into the host cell to express the protein.

The plasmid may be a bacterial cloning vector. The plasmid may include a site that allows DNA to be inserted, for example, a multiple cloning site or a polylinker including several commonly used restriction sites to which DNA fragments may be ligated. After the gene of interest is inserted, the plasmids are introduced into bacteria by transformation/transfection. The plasmids may further include a selectable marker, for example, an antibiotic resistance gene, which confers on the transfected bacteria an ability to survive and proliferate in a selective growth medium containing the particular antibiotic. The transfected bacterial cells are exposed to the selective media, and only those cells containing the plasmid survive. In this way, the antibiotic acts as a filter to select only those bacterial cells containing the plasmid DNA. The vector may also include other marker genes or reporter genes to facilitate selection of cells containing a plasmid with the cloned target gene insert. Thereafter, bacteria containing the plasmid may be grown in large amounts, harvested, and the plasmid isolated using various methods of plasmid preparation.

A plasmid cloning vector may be used to clone DNA fragments of about 15 kilobase pairs (kbp) or less. The vector may be a commercially available vector, for example, a pBBR112, pBR322, pUC, or TOPO cloning vector, but is not limited thereto.

The target gene may encode a target protein. The target gene may be a gene which is different from the gene which was linked with the promoter when the promoter was naturally occurring in an original cell. For example, the target gene may be a heterologous gene. A "heterologous gene" refers to a gene that originates from a source foreign to the host cell or, if from the same source, is modified from its original form.

The target gene may encode a target protein from the genus *Paracoccus*. In an aspect, the target gene encodes a target protein from *Paracoccus versutus*.

The gene encoding the target product may be a gene encoding monomer red fluorescent protein (mRFP) having the amino acid sequence of SEQ ID NO: 3. The target gene encoding the target protein may be a gene encoding the mRFP protein, and may have the nucleotide sequence of SEQ ID NO: 4. The isolated polynucleotide may be recombinant, artificial synthetic, or artificial semisynthetic.

Another aspect provides a recombinant host cell including the isolated polynucleotide including the promoter region including the nucleotide sequence of SEQ ID NO: 1. The isolated polynucleotide may be introduced into the host cell, i.e., introduced from the outside of the host cell. A "recombinant host cell" refers to a cell into which the isolated polynucleotide has been introduced and which replicates the polynucleotide or expresses a peptide or protein encoded by the polynucleotide.

The host cell may be a Gram-negative or Gram-positive bacterium. The Gram-negative bacterium may be a bacterium of the genus *Paracoccus* or *Escherichia*. The Gram-positive bacterium may be a bacterium of the genus *Bacillus*. The host cell may be *Paracoccus versutus*, *Bacillus bombysepticus*, or *Escherichia coli*. The host cell may be different from the cell from which the promoter is derived, for example, the host cell may belong to a different species from within the same genus or may be a host cell from a different genus.

In the recombinant host cell, the polynucleotide may be a vector. In the polynucleotide, the target gene may be operably linked to the promoter region. The target gene may encode a target protein. The target gene may encode a target protein of a bacterium from the genus *Paracoccus*, for example, *Paracoccus versutus*. The isolated polynucleotide may be recombinant, artificial synthetic, or artificial semisynthetic.

The vector may be introduced (e.g., transformed/transfected) into the host cell, for example, to facilitate cloning of the target gene. The vector may be introduced into the host cell, for example, to express the target gene. The introduction of the vector into the host cell may be performed by applying appropriate standard techniques, depending on the host cell. The introduction of the vector may be performed, for example, by electroporation, heat-shock, calcium phosphate ($CaPO_4$) precipitation, calcium chloride ($CaCl_2$) precipitation, microinjection, a polyethylene glycol (PEG) method, a DEAE-dextran method, a cationic liposome method, a lithium acetate-DMSO method, or a combination thereof.

In the vector introduced to the host cell, for example, a gene involved in the production of the target protein may be operably linked downstream of the promoter or a variant thereof. The vector may further include a replication origin, a promoter control site, a ribosome binding site, a transcription termination site, a selection marker, or a combination thereof, in addition to the promoter or variant thereof and the target gene. The host cell may express the production gene operably linked to the promoter or variant thereof, for example, under anaerobic conditions. For example, the gene may be highly expressed under aerobic conditions and may also maintain a relatively high level of gene expression under anaerobic conditions. The expression level of the gene may be, for example, 32 times greater, based on the amount of mRNA, under aerobic conditions as compared to expression level of the gene when operably linked with the tac promoter.

Still another aspect provides a method of expressing the target gene, the method including culturing the recombinant host cell including the isolated polynucleotide including the promoter region including the nucleotide sequence of SEQ ID NO: 1 and the target gene operably linked to the promoter region, under conditions in which the target gene is expressed.

The method includes culturing the recombinant host cell including the isolated polynucleotide including the promoter region including the nucleotide sequence of SEQ ID NO: 1 and the target gene operably linked to the promoter region, such that the target gene is expressed. The recombinant host cell is the same as described above.

In the method, the recombinant host cell may be a Gram-negative or Gram-positive bacterium. The Gram-negative bacterium may be a bacterium of the genus *Para-*

*coccus* or *Escherichia*. The Gram-positive bacterium may be a bacterium of the genus *Bacillus*. The recombinant host cell may be *Paracoccus versutus, Bacillus bombysepticus*, or *Escherichia coli*.

The target gene may encode a target protein. The target gene may encode a protein of the genus *Paracoccus*, for example, *Paracoccus versutus*. The isolated polynucleotide may be recombinant, artificial synthetic, or artificial semi-synthetic. In the recombinant host cell, the isolated polynucleotide may be a vector. In the polynucleotide, the target gene may be operably linked to the promoter region.

The method may include, for example, culturing the vector-introduced recombinant host cells to produce a final product in a biosynthetic pathway involving the protein encoded by the target gene. The target gene may be, for example, involved in production of a product such as a protein, an L-amino acid, lactic acid, acetic acid, succinic acid, or a combination thereof.

Therefore, the method may be used to produce the final product of a biosynthetic pathway, for example, a product such as a protein, an L-amino acid, lactic acid, acetic acid, succinic acid, or a combination thereof, under aerobic or anaerobic conditions. In the method, the product may be, for example, produced in a large amount under aerobic conditions, and also maintained in a relatively large amount under anaerobic conditions. The recombinant host cell may be, for example, *Paracoccus versutus* or *E. coli* that includes a vector in which the gene involved in the production of the final product is operably linked to the promoter having the nucleotide sequence of SEQ ID NO: 1 or a variant thereof.

The culturing of the recombinant host cell may be performed according to general methods known in the art. The culture medium may include a sugar source, an oil or a fat, a fatty acid, an alcohol, an organic acid, or a combination thereof. The sugar source may include, for example, a sugar and a carbohydrate, e.g., glucose, saccharose, lactose, fructose, maltose, starch, cellulose, or a combination thereof. The oil and fat may include, e.g., soybean oil, sunflower oil, castor oil, coconut oil, or a combination thereof. The fatty acid may include, e.g., palmitic acid, stearic acid, linolenic acid, or a combination thereof. The alcohol may include, e.g., glycerol, ethanol, or a combination thereof. An organic acid may include, e.g., acetic acid.

The culture medium may also include a nitrogen source, a phosphorous source, a metal salt, or a combination thereof. The nitrogen source may include, for example, peptone, a yeast extract, a meat extract, a malt extract, corn steep liquor, soy meal and urea, an inorganic compound such as ammonium sulfate, ammonium chloride, ammonium phosphate, ammonium carbonate, or ammonium nitrate, or a combination thereof. The culture medium may include as a phosphorous source, potassium dihydrogen phosphate, dipotassium hydrogen phosphate, a corresponding sodium-containing salt thereof, or a combination thereof.

The culture medium may include, for example, a metal salt, e.g., magnesium sulfate, iron sulfate, or a combination thereof which is essential for growth. Also, in the culturing, substances essential for growth, such as amino acids and vitamins, or suitable precursors may be added to the culture. A combination comprising at least one of the foregoing may also be used.

Each of the above-listed components may be added to the culture in a proper manner, for example, in a batch or continuous manner during the culturing.

The culturing may be performed under aerobic conditions.

According to an aspect, gene transcription may be efficiently initiated in the isolated polynucleotide.

According to another aspect, transcription of the target gene may be efficiently initiated in the recombinant host cell.

According to still another aspect, the target gene may be efficiently expressed in the method of expressing the target gene.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modifies the entire list of elements and does not modify the individual elements of the list.

The terminology used herein is for the purpose of describing particular embodiments only and is not intended to be limiting. As used herein, the singular forms "a," "an," and "the" are intended to include the plural forms, including "at least one," unless the content clearly indicates otherwise. "At least one" is not to be construed as limiting "a" or "an." "or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Hereinafter, the present disclosure will be described in more detail with reference to the Examples. However, these Examples are for illustrative purposes only, and the scope of the present disclosure is not intended to be limited by these Examples.

Example 1: Exploration and Identification of *Paracoccus versutus* Promoter

In this Example, genes were selected from a denitrifying microorganism *Paracoccus versutus* (strain DSM 582) and putative promoters of each of the genes were isolated, respectively. Vectors including each promoter operably linked to a reporter protein-encoding gene was constructed, and each vector was introduced into the host strain to examine promoter strength.

(1) Exploration of Promoter

Polynucleotides which were considered to include a promoter were obtained from gene regions encoding glyceraldehyde-3-phosphate dehydrogenase (gapD), phosphoglycerate kinase (pgk), or phosphoenolpyruvate carboxykinase (pepck) of *Paracoccus versutus*. The promoter region was amplified by PCR using primers designed for in-fusion cloning, and then used for vector construction. The primer sets used for PCR amplification of the promoter regions of the gapD, pgk, and pepck genes were polynucleotides having the sequences of SEQ ID NOS: 5 and 6; SEQ ID NOS: 7 and 8; and SEQ ID NOS: 9 and 10, respectively.

(2) Construction of Vector

A vector including the obtained promoter polynucleotide was constructed. The vector was constructed as follows.

A pB-GAP vector was constructed as follows. A pBBR-122 vector (Mo Bi Tec) as a template and a primer set having the sequences of SEQ ID NOS: 11 and 12 were used to amplify the pBBR-122 vector. The genomic DNA of *Paracoccus versutus* strain was used as a template with the primer set of SEQ ID NOS: 5 and 6 to amplify the promoter region of the gapD gene. The primer set having the nucleotide sequences of SEQ ID NOS: 13 and 14 was used to amplify mRFP, which was then cloned into the amplified vector backbone using an In-fusion GD cloning kit (Takara), thereby constructing a pB-GAP vector.

The vector region was amplified using the pB-GAP vector as a template and a primer set of SEQ ID NOS: 11 and 12, and each of the promoter regions amplified using a primer set of SEQ ID NOS: 9 and 10 or a primer set of SEQ ID NOS: 7 and 8 were cloned using an In-Fusion GD cloning kit (Takara) to construct pB-PEPCK and pB-PGK vectors, respectively.

Figure 1:
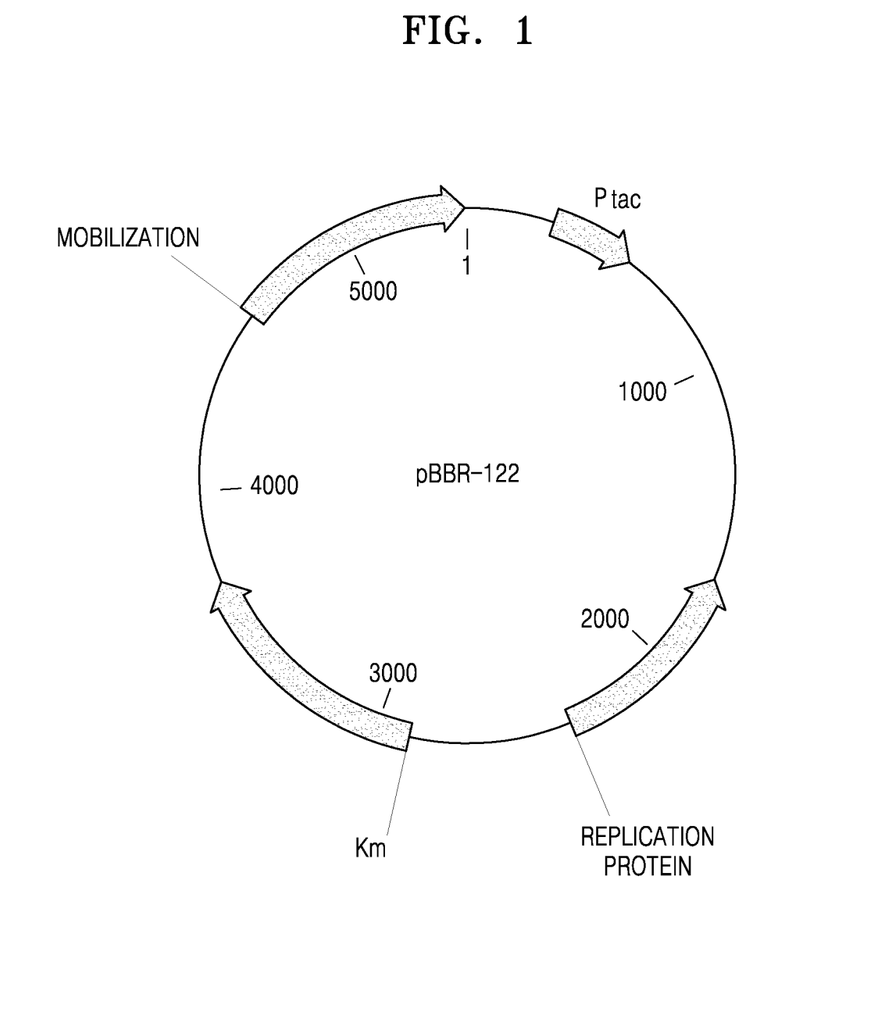
FIG. 1 illustrates a map of a pBBR-122 vector.

FIG. 1 illustrates a map of the pBBR-122 vector. mRFP represents monomeric red fluorescent protein (RFP).

Figure 2:
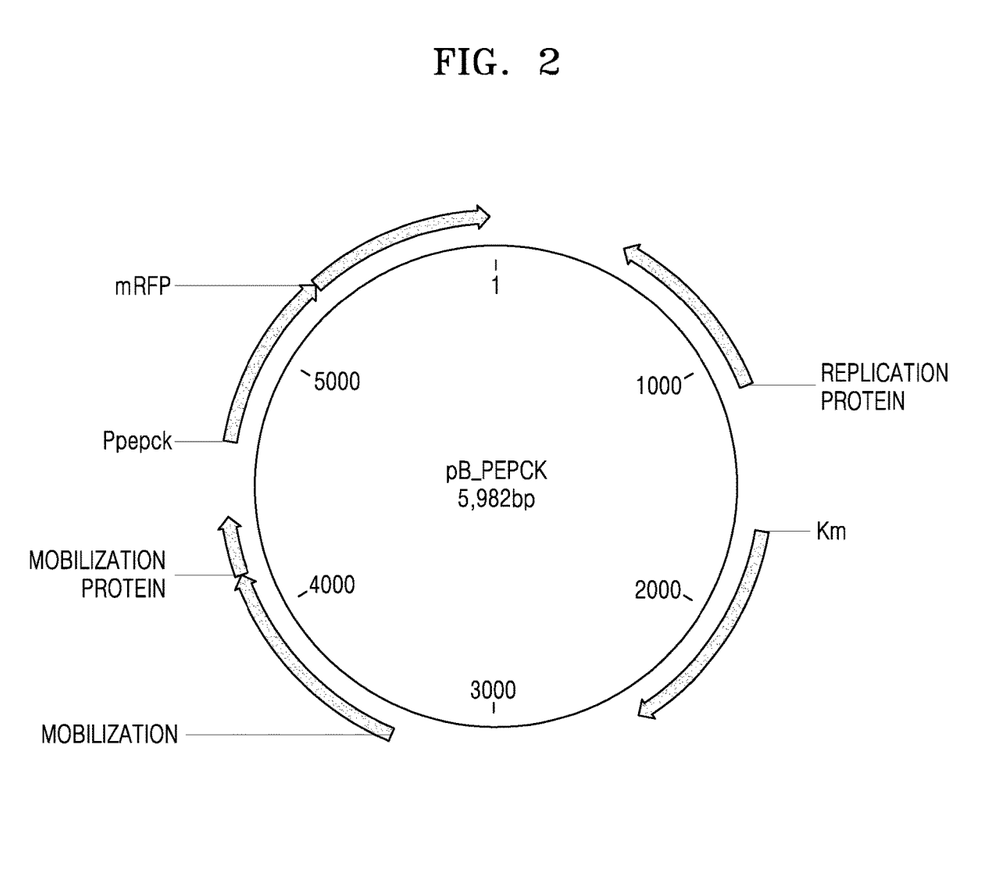
FIG. 2 illustrates a map of a pB_PEPCK vector.

FIG. 2 illustrates a map of the pB_PEPCK vector.

(3) Comparative Evaluation of Promoter Performance

Vectors including the mRFP gene downstream of the promoter polynucleotides of three genes derived from *Paracoccus versutus* were constructed as described in (2), and each of the vectors was introduced into *Paracoccus versutus* strain. The introduction was performed by electroporation. As control groups, buffer and pBBR-122 vector were introduced into *Paracoccus versutus* strain in the same manner, respectively.

Figure 3:
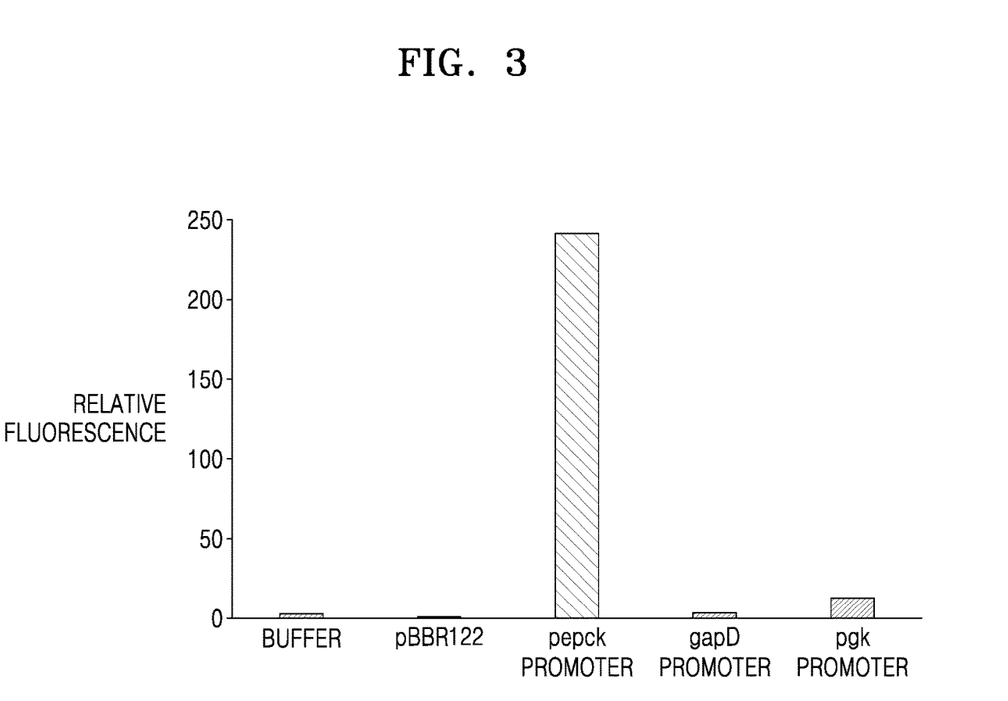
FIG. 3 is a graph of relative fluorescence versus test sample, which shows the results of measuring fluorescence emitted from mRFP protein expressed by each promoter in *Paracoccus versutus*.

Each strain was cultured in an LB medium under conditions of 30° C. and with shaking at 230 rpm, for 18 hr. After culturing, the strain was isolated and quantified at A600 of 1. Fluorescence was measured at excitation of 485 nm and emission of 590 nm using Spectramax M5 to determine mRFP expression. The results are shown in Table 1 and FIG. 3. FIG. 3 shows results of measuring fluorescence emitted from mRFP protein expressed by each promoter in *Paracoccus versutus*.

TABLE 1

| Sample | PBS buffer | pBBR122 | pepck promoter (pB_PEPCK) | gapD promoter (pB-GAP) | pgk promoter (pB-PGK) |
|---|---|---|---|---|---|
| Relative fluorescence | 3.13 | 1.78 | 242.08 | 4.35 | 13.75 |

As shown in Table 1 and in FIG. 3, PBS buffer, pBBR122, gapD promoter, and pgk promoter showed very low mRFP fluorescence, whereas the pepck promoter showed significantly high fluorescence. These results indicate that the pepck promoter is a very strong promoter capable of efficiently expressing a foreign (heterologous) target protein.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. An isolated polynucleotide comprising a promoter region comprising the nucleotide sequence of SEQ ID NO: 1 or SEQ ID NO:2, wherein the isolated polynucleotide is a vector.

2. The isolated polynucleotide of claim 1, wherein a target gene is operably linked to the promoter region.

3. The isolated polynucleotide of claim 2, wherein the target gene encodes a target protein.

4. The isolated polynucleotide of claim 3, wherein the target protein comprises the amino acid sequence of SEQ ID NO: 3.

5. A recombinant host cell comprising the isolated polynucleotide of claim 1.

6. The recombinant host cell of claim 5, wherein the recombinant host cell is a bacterial cell.

7. The recombinant host cell of claim 5, wherein the recombinant host cell is different from the cell from which the promoter is derived.

8. The recombinant host cell of claim 5, wherein the recombinant host cell is a bacterial cell of the genus *Paracoccus* or the genus *Escherichia*.

9. The recombinant host cell of claim 7, wherein the recombinant host cell is *Paracoccus versutus* or *Escherichia coli*.

10. The recombinant host cell of claim 5, wherein a target gene is operably linked to the promoter region.

11. The recombinant host cell of claim 10, wherein the target gene encodes a target protein.

12. The recombinant host cell of claim 10, wherein the target protein comprises the amino acid sequence of SEQ ID NO: 3.

13. A method for expressing a target gene, the method comprising:
culturing the recombinant host cell of claim 10, under conditions in which the target gene is expressed.

14. The method of claim 13, wherein the recombinant host cell is a bacterial cell.

15. The method of claim 13, wherein the target gene encodes a target protein.

16. The method of claim 13, wherein the culturing is performed under aerobic conditions.

* * * * *